US007674227B1

(12) United States Patent
Cienfuegos

(10) Patent No.: US 7,674,227 B1

(45) **Date of Patent: *Mar. 9, 2010**

(54) ILLUMINATED DISPLAY SYSTEM

(76) Inventor: Juan Enrique Cienfuegos, 13522 Shelbritt Rd., San Antonio, TX (US) 78249

( * ) Notice: Subject to any disclaimer, the term of this patent is extended or adjusted under 35 U.S.C. 154(b) by 109 days.

This patent is subject to a terminal disclaimer.

(21) Appl. No.: 11/998,951

(22) Filed: Dec. 3, 2007

Related U.S. Application Data

(62) Division of application No. 11/291,391, filed on Dec. 1, 2005, now Pat. No. 7,326,179.

(60) Provisional application No. 60/633,046, filed on Dec. 2, 2004.

(51) Int. Cl.
*A61B 5/00* (2006.01)

(52) U.S. Cl. ........................ 600/300; 362/231; 362/253

(58) Field of Classification Search ................. 362/800, 362/231, 253; 600/300
See application file for complete search history.

(56) References Cited

U.S. PATENT DOCUMENTS 5,070,437 A 12/1991 Roberts, Sr.
5,149,190 A 9/1992 MacKenzie
5,568,971 A 10/1996 Jewell
5,670,942 A 9/1997 Lewis
5,683,164 A 11/1997 Chien
6,086,218 A 7/2000 Robertson
6,305,819 B1 10/2001 Chen
6,431,728 B1 8/2002 Fredericks et al.
6,626,557 B1 9/2003 Taylor
7,218,241 B2 5/2007 Kessel et al.
7,326,179 B1 * 2/2008 Cienfuegos ................ 600/300

* cited by examiner

*Primary Examiner*—Anabel M Ton
(74) *Attorney, Agent, or Firm*—Rafael V. Baca; Baca Law Firm, PLLC

(57) ABSTRACT

An illuminated display system and method for prioritizing medical care administered to an injured user, such a soldier in battlefield settings. The illuminated display system may be applied to triage scenarios whereby illuminated signals visually provide the triage status of an injured user at a distance and in low-visibility settings. In particular, the illuminated display system includes a plurality of light emitters. Each light emitter from the plurality of light emitters provides a different predetermined wavelength of light than the other light emitters from the plurality of light emitters. In operation, each respective predetermined wavelength of light provides information relating to the degree of injury or other information associated with the user such that a desired light emitter is selected to display the desired wavelength and, ultimately, the desired information.

20 Claims, 10 Drawing Sheets

ILLUMINATED DISPLAY SYSTEM

CROSS REFERENCE TO RELATED APPLICATIONS

This application is a Divisional of Non-Provisional application Ser. No. 11/291,391, filed Dec. 1, 2005, now U.S. Pat. No. 7,326,179 which claims benefit under 35 U.S.C. §119(e) from prior U.S. Provisional Patent Application Ser. No. 60/633,046 filed on Dec. 2, 2004 entitled "An Illuminated Display System and Method of Use", by inventor Juan Enrique Cienfuegos, the entire disclosure of which is hereby incorporated by reference as if fully set forth herein.

BACKGROUND OF THE INVENTION

1. Field of the Invention

The present invention generally relates to an illuminated display system for placement on a user or receiving object. More particularly, but not by way of limitation, the present invention relates to a system and method for visually displaying information from a selection of light signals whereby the information, for example, may be used for prioritizing the degree of medical care administered to a user.

2. Description of the Related Art

In the past, the concept of assessing an individual's medical condition and prioritizing that individual's need for medical care with respect to others requiring assistance is a concept commonly known as "Triage". Triage is one of the first applications of medical care applied to an individual and is often used as a technique to address the most seriously injured first. The triage concept is applied to humans and animals alike and in a variety of patient care settings including hospital emergency rooms, in the field with emergency medical service providers such as with natural disaster conditions and in battlefield settings.

Generally, triage techniques attempt to sort patients into categories for transport and immediate medical treatment. Triage is administered oftentimes in imperfect conditions where immediate medical care is limited, time is critical, and patients are prone to inaccurately advocating their precise medical condition.

Triage assessors generally tag patients according to the degree of injury. Many typical examples of triage tags are based on color coded information cards by which an assessor provides a written description of the patient's condition on that paper card.

Illustratively, in a battlefield setting, either a combat medic or corpsman provides triage assessments to injured soldiers on the battlefield. In practice, a medic is personally at risk from being fired on or the hazardous conditions associated with the battlefield. A medic's triage assessment must not only be accurate, but must be quickly provided so as not jeopardize the health of the injured soldier or of the medic themselves. Many times, a medic is not given the opportunity to provide a written description or even color code an injured soldier accordingly. Furthermore, battlefield conditions hinder one's ability to accurately read a corresponding triage card. Illustratively, smoke, dust, and changing weather conditions obscure one's ability to determine the triage status of an injured solider at a distance. Moreover, conditions such as complete darkness, underwater settings or in buried conditions could render the determination of written information on one's triage card as improbable. Unfortunately, there is no known device or method for quickly and accurately providing triage status at a distance, such as status of an injured soldier in various battlefield settings.

Therefore, a need exists for a system and method for placement on a user that quickly and accurately provides information relating to the degree of injury of the user. There is also a need for a system and method for quickly and accurately providing information including triage information in varied visibility conditions and at a distance. Many other problems and disadvantages of the prior art will become apparent to one skilled in the art after comparing such prior art with the present invention as herein described.

SUMMARY OF THE INVENTION

Aspects of the invention are found in an illuminated display system for prioritizing medical care administered to an injured user. In one aspect, the illuminated display system is applied in triage settings whereby illuminated signals visually provide the triage status of an injured user at a distance and in low-visibility settings such as, among others, in complete darkness, in smoke, fog or dust, episodes of adverse weather such as snow or rain or in areas of dense undergrowth, snow cover, or while submerged.

In particular, the illuminated display system includes a base assembly. The base assembly features a base body having a first portion and a second portion. In one aspect, a fastening interface is positioned on the second portion whereby the fastening interface operatively couples the illuminated display system to the user.

The illuminated display system, in one aspect, further includes a display interface disposed on the first portion of the base body. The display interface includes a plurality of light emitters, such as, among others, light emitting diodes and organic light emitting diodes. In one aspect, each light emitter from the plurality of light emitters provides a different predetermined wavelength of light than the other light emitters from the plurality of light emitters. In operation, each respective predetermined wavelength provides information relating to the degree of injury of the user.

The illuminated display system includes a dial assembly operatively coupled to the base assembly. The dial assembly includes a dial lens and a selector. The dial lens is positioned adjacent to the display interface. The selector activates a desired light emitter from the plurality of light emitters by applying a voltage to the desired light emitter for illumination thereof.

In one aspect, the illuminated display assembly further includes a control system operatively coupled to the plurality of light emitters. In one aspect, among others, the control system adjusts the intensity of light produced by at least one light emitter of the plurality of light emitters. In one aspect, the control system adjusts the duration of light signal produced by at least one light emitter from the plurality of light emitters.

In one aspect, an illuminated display system is provided for prioritizing medical care administered to an injured soldier in battlefield settings. The illuminated display system includes a base assembly featuring a base body. In one aspect, the base body is divided into a first portion and a second portion. The illuminated display system may optionally include a fastening interface positioned at the second portion to operatively couple with the injured soldier.

In one aspect, the illuminated display system includes a display interface disposed on the first portion of the base body. The display interface includes a plurality of light emitters. Each light emitter from the plurality of light emitters provides a different predetermined wavelength of light than the other light emitters from the plurality of light emitters. In operation, each respective predetermined wavelength provides information relating to the degree of injury of the soldier.

The illuminated display system includes a dial assembly operatively coupled to the base assembly. The dial assembly features a dial lens positioned adjacent to the display interface. In one aspect, the dial lens includes a combination of light filters and light modifiers. The dial assembly further includes a selector for applying a voltage to the desired light emitter for illumination thereof as related to the degree of injury of the soldier.

Illustratively, in one aspect, a method is provided for prioritizing medical care administered to an injured soldier in battlefield settings. The method includes the step of administering a brief clinical assessment of the injured soldier. An illuminated display system is secured to the injured soldier. A selector from the illuminated display system applies a voltage to the desired light emitter for activation thereof. The light emitter is illuminated at desired predetermined wavelength to provide information related the degree of injury of the soldier.

Other aspects, advantages, and novel features of the present invention will become apparent from the detailed description of the present invention when considered in conjunction with the accompanying drawings.

BRIEF DESCRIPTION OF THE DRAWINGS

The present invention is illustrated by way of example and not by limitation in the accompanying figures, in which like references indicate similar elements, and in which.

Skilled artisans appreciate that elements in the Figures are illustrated for simplicity and clarity and have not necessarily been drawn to scale. For example, the dimensions of some of the elements in the Figures may be exaggerated relative to the other elements to help improve understanding of the embodiments of the present invention.

DETAILED DESCRIPTION

For a more complete understanding of the present invention, preferred embodiments of the present invention are illustrated in the Figures. Like numerals being used to refer to like and corresponding parts of the various accompanying drawings. It is to be understood that the disclosed embodiments are merely exemplary of the invention, which may be embodied in various forms.

Figure 1:
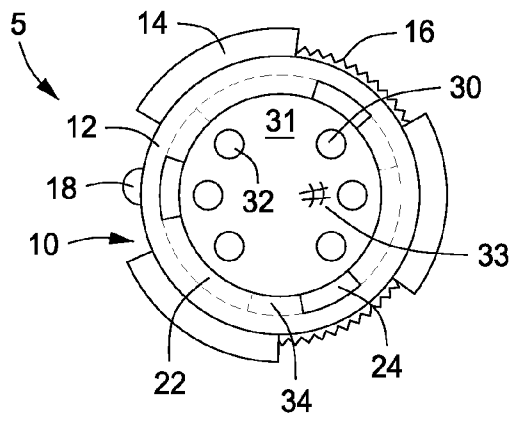
FIG. 1 is an orthographic view from the top illustrating an illuminated display system for placement on an user according to the present invention, the illuminated display system includes a plurality of light emitters that individually emit a predetermined wavelength band relating to the user's status.

FIG. 1 illustrates one aspect, among others, of an illuminated display system 5 for placement on a user or receiving object. Generally, an illuminated display system provides information associated with the user or receiving object through light emission at various wavelengths. In this application, the terms "user" and "receiving element" respectively refer to a living being and non-living object by which an illuminated display system is attached to. For example, an illuminated display system provides information relating to the injury of a user in a triage situation such as the degree of injury, the nature of injury, and likelihood of survival.

Specifically as viewed from the top in FIG. 1, the illuminated display system 5 includes a plurality of light emitters 32. At least one light emitter from the plurality of light emitters 32 is selected for illumination thereof according to the injury of the user. The illuminated display system 5 may then be attached to the user or receiving object while operatively illuminated. Illumination of a desired light emitter provides information describing the current status of the user, such as the kind of injury received, the likelihood for injury recovery or the location of the injured party.

The illuminated display system 5 includes a base assembly 30. The base assembly 30 includes a display interface 31. As shown in FIG. 1, the plurality of light emitters 32 are incorporated with the display interface 31.

The illuminated display system 5 includes a dial assembly 10. The dial assembly 10 is operatively coupled to the base assembly 30.

The illuminated display system 5 further includes a selector 18. As shown in the embodiment of FIG. 1, the selector 18 is disposed on the dial assembly 10. Operatively, the dial assembly 10 rotates about the base assembly 30 so as to position the selector 18 adjacent to a desired light emitter from the plurality of light emitters 32 located on the display interface 31. The selector 18 is thus manipulated to either engage or disengage a desired light emitter from the plurality of light emitters 32. In one exemplary embodiment, the illuminated display system 5 is rendered in a consistent, electrically "off" position until the selector 18 engages with a light emitter from the plurality of light emitters 32. In this manner, the illuminated display system 5 will be illuminated as desired.

Each light emitter from the plurality of light emitters 32 radiates a different wavelength of light than other light emitters from the plurality of light emitters 32. In this manner, each respective predetermined wavelength of light provides information associated with the status of a user or receiving object. For example, each different light emitter provides correspondingly different information as related to the degree of injury of an injured user, such as a soldier. Those of ordinary skill in the art will readily recognize that each respective predetermined wavelength represents corresponding predetermined information to be conveyed by the user. Ultimately, as a desired light emitter is selectively illuminated, the illuminated display system 5 when placed on an injured user facilitates quick, efficient prioritization of the user for future treatment and transport in a triage setting.

In one exemplary embodiment, the plurality of light emitters 32 includes a light emitting diode for emitting light at various wavelengths along the entire electromagnetic spectrum. In particular, the plurality of light emitters 32 includes a light emitting diode for providing an infrared wavelength band of light. The plurality of light emitters 32 includes a light emitting diode for providing an intermittent infrared light emission. The plurality of light emitters 32 includes a light emitting diode for radiating a wavelength of red visible light. The plurality of light emitters 32 includes a light emitting diode for supplying a green wavelength band of visible light. The plurality of light emitters 32 further includes a light emitting diode for generating a blue wavelength band of visible light. In one exemplary embodiment, the plurality of light emitters 32 may include an single light emitting diode arranged on the display interface 31 for providing blue, green, and red visible light in addition to an infrared band and an intermittent band of infrared light.

Those of ordinary skill in the art will readily recognize other widely known light emitters for selective illumination about the display interface 31 and emission of light at various wavelengths. Illustratively, in one exemplary embodiment, the plurality of light emitters 32 includes inorganic light emitting diodes. In one exemplary embodiment, the plurality of light emitters 32 includes organic light emitting diodes. In one exemplary embodiment, the plurality of light emitters 32 includes a combination of inorganic and organic light emitting diodes. In one exemplary embodiment, the plurality of light emitters 32 may include an incandescent light emitter. In one exemplary embodiment, the plurality of light emitters 32 includes a fluorescent light emitter.

Referring to the embodiment of FIG. 1, the dial assembly 10 of the illuminated display system 5 is configured to accommodate manual rotation of the selector 18 with respect to the display interface 31. Illustratively, in one exemplary embodiment, the dial assembly 10 includes a dial body 12. The dial body 12 may optionally include dial tabs 14 extending outwardly from the dial body 12. By projecting outwardly from the dial body 12, the dial tabs 14 operatively provide enhanced rotational grip of the dial assembly 10, such as for example facilitating rotation of the dial assembly 10 while wearing gloves. Moreover, through the sense of touch, the dial tabs 14 provide a means for readily identifying the location of the selector 18 without visual confirmation.

As shown in FIG. 1, at least one grip element 16 may be provided on the dial body 12 between adjacent dial tabs 14. Similar to the dial tabs 14, the at least one grip element 16 facilitates manual rotation of the dial assembly 10 about the display interface 31 and for identifying the selector's 18 location without visual confirmation.

The dial assembly 10 for the embodiment of FIG. 1 further includes a dial lens 33. The dial lens 33 in FIG. 1 is positioned above the display interface 31. In one exemplary embodiment, the dial lens 33 is releasable from the dial assembly 10. Accordingly, the dial body 12 defines a series of gateway notches 24. The gateway notches 24 engage with a corresponding series of lens tabs 34 extending outwardly from the dial lens 33. As shown in FIG. 1, the dial body 12 further includes a support channel 22. The support channel 22 extends outwardly from the dial body 12 toward the base assembly 30. Operatively, the lens tabs 34 are secured between the dial body 12 and the support channel 22.

Illustratively, to secure the dial lens 33 to the dial assembly 10, the lens tabs 34 of the dial lens 33 are initially passed through the respective gateway notches 24. After passing through the gateway notches 24, the lens tabs 34 slide and lock in place atop the support channel 22 between the dial body 12 and the support channel 22. Those of ordinary skill in the art will readily recognize other well known means for securing the dial lens 33 to the dial assembly 10 such as with screw threading, by vacuum pressure, adhesives, and locks. Moreover, in one exemplary embodiment, a hermetic seal may be disposed on the support channel 22 for engagement with the dial lens 33. For example, an O-ring seal may be placed on the support channel 22 so that the lens tabs 34 rest atop the O-ring seal as the dial lens 33 is secured to the dial assembly 10.

Figure 2:
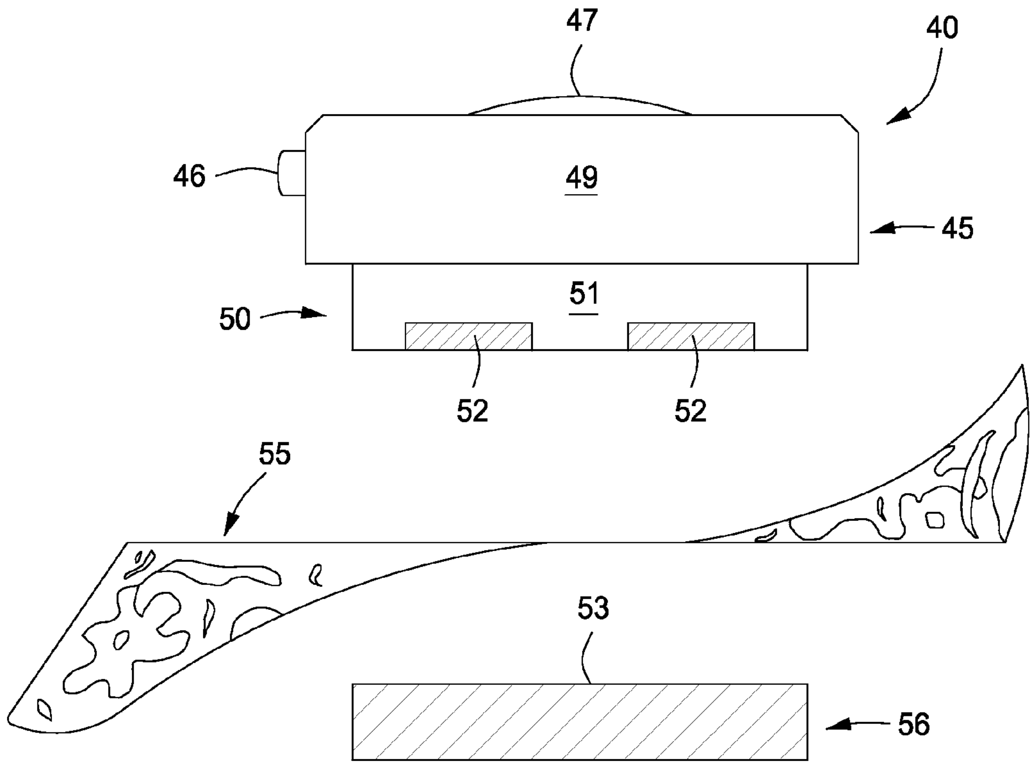
FIG. 2 is an exploded orthographic view illustrating one exemplary embodiment of an illuminated display system for operative engagement with a user, the illuminated display system includes a fastening interface and a clamp member whereby an article of clothing worn by the user is operatively fixed between the fastening interface and the clamp member.

FIG. 2 illustrates one exemplary embodiment of an illuminated display system 40 for engagement with a receiving element 55. Specifically, in one exemplary embodiment, the receiving element 55 comprises an article of clothing worn by an injured user, such as a soldier's camouflage uniform shown in FIG. 2.

The illuminated display system 40 of FIG. 2 includes a base assembly 50 and a dial assembly 45. The dial assembly 45 is coupled to the base assembly 50. The base assembly 50 includes a base body 51 having a top portion and a bottom portion. The base body 51 includes a display interface (not shown) disposed on the top portion of the base body 51. The display interface includes a plurality of light emitters. Each light emitter from the plurality of light emitters provides a different predetermined wavelength of light than the other light emitters from the plurality of light emitters. In this application, the term "light" refers to the entire electromagnetic spectrum of light whereas the term "visible light" refers to a wavelength range of the electromagnetic spectrum that is observable to the human eye. Each respective predetermined wavelength of light provides information relating to a user's status, such as information relating to the degree of injury of the user in a triage setting.

As shown in FIG. 2, the dial assembly 45 includes a dial lens 47. In operation, the dial lens 47 is positioned above the display interface.

A selector 46 is positioned on the dial assembly 45. The selector 46 electrically activates a desired light emitter from the plurality of light emitters. Specifically, the dial assembly 45 operatively moves the selector 46 relative to the display interface. The selector 46 is ultimately positioned adjacent to a desired light emitter from the plurality of light emitters. The selector 46 effectively applies a voltage to the desired light emitter for illumination thereof. In one exemplary embodiment, the selector 46 comprises a spring-loaded button for opening and closing a desired electrical circuit for activating a desired light emitter. It should be added that the plurality of light emitters in one exemplary embodiment are rendered in a consistently "off" electrical configuration until the selector 46 electrically activates at least one light emitter.

Referring to the embodiment of FIG. 2, the base assembly 50 includes a fastening interface 52. The fastening interface 52 is positioned about the bottom portion of the base body 51. In operation, the fastening interface 52 secures the illuminated display system 40 to a user or receiving object. In one exemplary embodiment, the fastening interface 52 includes permanent magnet, such as a rare earth magnet. Illustratively, in one exemplary embodiment, the fastening interface 52 comprises a Neodymium (Nd)-Iron (Fe)-Boron (B) supermagnet.

The illuminated display system 40 further includes a clamp member 56. The clamp member 56 is operatively coupled to the fastening interface 52 of the base assembly 50. In one exemplary embodiment, the clamp member 56 may be composed of a magnetically attractive material such as iron or material comprising a permanent magnet.

The clamp member 56 of FIG. 2 includes a clamp body 53. In operation, the clamp body 53 is placed beneath the receiving element 55. In particular, the clamp body 53 may be placed beneath the clothing of the user, such as the uniform of an injured soldier.

Operatively, the fastening interface 52 becomes magnetically attracted to the clamp member 56 such that the illuminated display system 40 is secured in place onto the receiving element 55. Accordingly, the illuminated display system 40 is secured to the outer portion of a soldier's uniform so that the illuminated display system 40 will not separate from the uniform during transport of the injured soldier while emitting a light signal relating to the degree of injury of the soldier.

In one exemplary embodiment, the clamp body 53 of FIG. 2 may comprise a rare earth permanent magnet. Accordingly, the magnetic attractiveness between permanent magnets comprising both the fastening interface 52 and the clamp member 56 is characteristically amplified so as to firmly secure the illuminated display system 40 to the receiving element 55.

Figure 3:
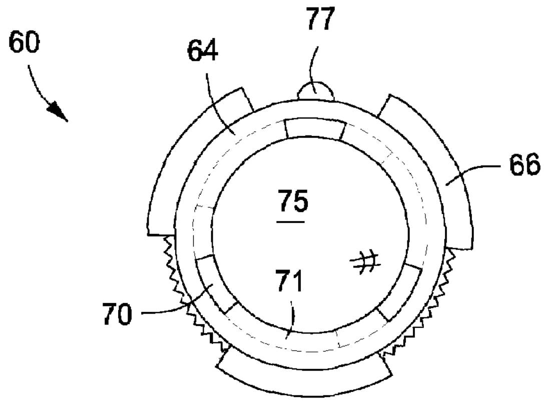
FIG. 3 is an orthographic view from the top illustrating one exemplary embodiment of a dial assembly of an illuminated display system.

FIG. 3 is a top view illustrating one exemplary embodiment of a dial assembly 60 for an illuminated display system. The dial assembly 60 includes a dial body 64 and dial tabs 66 extending outwardly from the dial body 64. As shown in FIG. 3, a selector 77 is positioned on the dial body 64 between a pair of adjacent dial tabs 66.

The dial assembly 60 further includes a dial lens 75. In operation, the dial lens 75 is secured onto a support channel 71 provided by the dial body 64. The dial lens 75 is releasable from the dial body 64 through a series of gateway notches 70 provided by the dial body 64.

Figure 4:
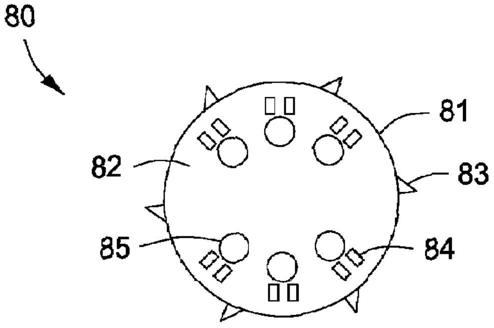
FIG. 4 is an orthographic view from the top illustrating one exemplary embodiment of a base assembly of an illuminated display system, the base assembly including a plurality of light emitters.

FIG. 4 is a top view illustrating one exemplary embodiment of a base assembly 80 of an illuminated display system. The base assembly 80 includes a base body 81 and a display interface 82 provided by the base body 81. The display interface 82 includes a plurality of light emitters 85 arranged about the display interface 82.

As shown in the embodiment of FIG. 4, a series of contact terminal units 84 are positioned near each respective light emitter from the plurality of light emitters 85 on the display interface 82. Operatively, as a selector is positioned near a desired light emitter from the plurality of light emitters, the selector electrically closes a respective contact terminal unit 84 so that a voltage is applied to the desired light emitter for illumination thereof.

The base assembly 80 further includes a series of locator teeth 83. The locator teeth 83 are positioned about the periphery of the display interface 82. Operatively, as the dial assembly 60 rotates about the display interface 82, the locator teeth

83 contact a dial body from a dial assembly. As shown in FIG. 4, the locator teeth 83 may be configured to permit rotation in one direction. Illustratively, as shown in FIG. 4, the locator teeth 83 are cam-shaped to facilitate clockwise rotation of the dial assembly with respect to the display interface 82.

The locator teeth 83 are positioned about the display interface 82 in intervals. In one exemplary embodiment, the locator teeth 83 are positioned adjacent to each contact terminal unit from the series of contact terminals units 64. Accordingly, a locator tooth positioned adjacent to a respective light emitter provides physical identification of the location of a particular light emitter with respect to the display interface without visual confirmation through indications of touch and, optionally, of sound. Optionally, a terminus locator tooth may be provided on the base body 81 to either prevent or hinder further rotation of the dial assembly 60 past the terminus locator tooth. In this manner, the terminus locator tooth indicates completion of a full dial assembly turn cycle. Those of ordinary skill in art will readily recognize other suitable means well known in the industry for confirming the location of the dial assembly relative to the display interface, such as drop notches and pin notches.

In particular, as a selector rotates toward a desired contact terminal, a dial assembly contacts the base body 81 at a locator tooth positioned adjacent to a desired light emitter. The interactive feeling of contact between the dial assembly and the locator tooth ultimately ensures that a selector is sufficiently positioned to permit electrical operation of the desired light emitter at a corresponding contact terminal. Optionally, the locator tooth may be configured to permit a sonic confirmation of the contact between the dial assembly and the locator tooth such as a ratcheting or clicking sound.

Figure 5:
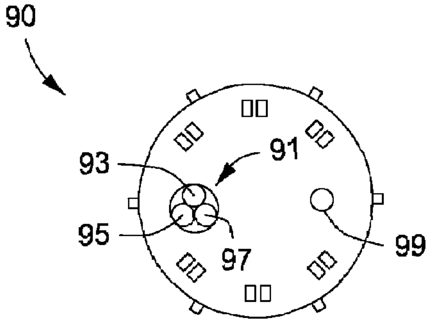
FIG. 5 is an orthographic view from the top illustrating one exemplary embodiment of a base assembly of an illuminated display system, the base assembly including a plurality of light emitters.
Figure 6:
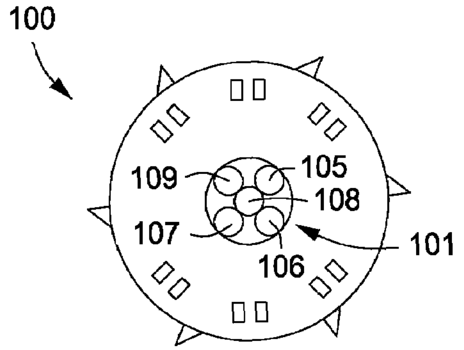
FIG. 6 is an orthographic view from the top illustrating one exemplary embodiment of a base assembly of an illuminated display system, the base assembly including a plurality of light emitters.
Figure 7:
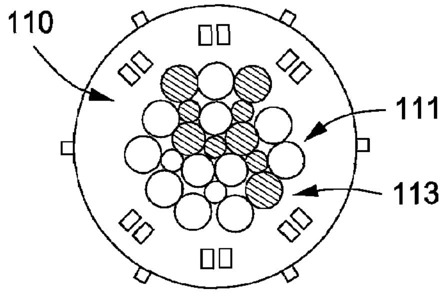
FIG. 7 is an orthographic view from the top illustrating one exemplary embodiment of a base assembly of an illuminated display system, the base assembly including a plurality of light emitters.

FIGS. 5-7 illustrate various arrangements of light emitters with respect to a base assembly. Accordingly, each light emitter shown in FIGS. 5-7 may include an inorganic light emitting diode, an organic light emitting diode, or a combination thereof.

Specifically, FIG. 5 shows a base assembly 90. The base assembly 90 as shown includes four light emitters. In particular, the base assembly 90 includes a blue light emitting diode 93, a green light emitting diode 95, and a red light emitting diode 97 each for emission of colored light in the visible spectrum. To facilitate ease of interchangeability, the light emitting diodes 93, 95, 97 may be bundled within an emitter module 91. In one exemplary embodiment, the base assembly 90 may include a single, "multi-color" light emitting diode, such as a light emitting diode for providing red, orange and yellow light or, alternatively, red and infrared light.

The base assembly 90 further includes an infrared light emitting diode 99. Operatively, the infrared light emitting diode 99 may emit light continuously and at predetermined intervals.

FIG. 6 illustrates one exemplary embodiment of a base assembly 100. In particular, the base assembly 100 includes five light emitters. Each of the five light emitters may be optionally bundled in a light emitting module 101 to facilitate ease of interchangeability.

Illustratively, a first light emitting diode 105 supplies infrared light. A second light emitting diode 106 may provide intermittent infrared light. A third light emitting diode 107 generates red visible light. A fourth light emitting diode 108 radiates green visible light. A fifth light emitting diode 109 provides blue visible light.

FIG. 7 illustrates one exemplary embodiment of a base assembly 110. The base assembly 110 includes a plurality of light emitters. Specifically, the plurality of light emitters forms an emitter array 111. The emitter array 111 is characterized by closely-spaced, geometrical arrangement of light emitters. As shown in FIG. 1, the emitter array 111 may display alphanumeric information by selectively illuminating a combination of light emitting diodes. Accordingly, the alphanumeric characters "1*f*" shown in FIG. 7 are formed through the selective illumination of light emitting diodes from the emitter array 111.

Figure 8:
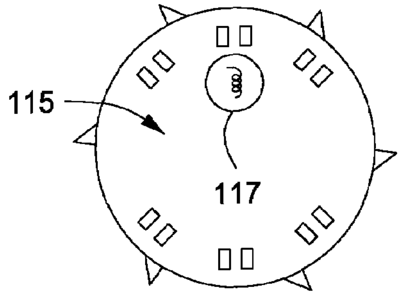
FIG. 8 is an orthographic view from the top illustrating one exemplary embodiment of a base assembly of an illuminated display system, the base assembly including a single light emitter.

FIG. 8 illustrates one exemplary embodiment of a base assembly 115. The base assembly 115 includes a single light emitter 117. The light emitter 117 of FIG. 8 radiates white light. In one exemplary embodiment, the single light emitter 117 comprises an incandescent light. In one exemplary embodiment, the single light emitter 117 comprises a fluorescent light. In one exemplary embodiment, the single light emitter 117 comprises a light emitting diode.

A dial lens from a lens assembly may filter various wavelengths of white light emitted from the light emitter 117 to obtain a desired wavelength such as blue visible light. The dial lens may include a plurality of filters arranged for manipulating the white light from the light emitter 117 to thus provide a desired light signal from a plurality of possible light wavelengths. Each light wavelength signifies different information relating to the status of a user, such as the degree of medical care required by an injured patient in a triage setting. Operatively, at least one light filter is positioned over the light emitter 117 to produce a resulting filtered light signal for providing predetermined information.

Figure 9:
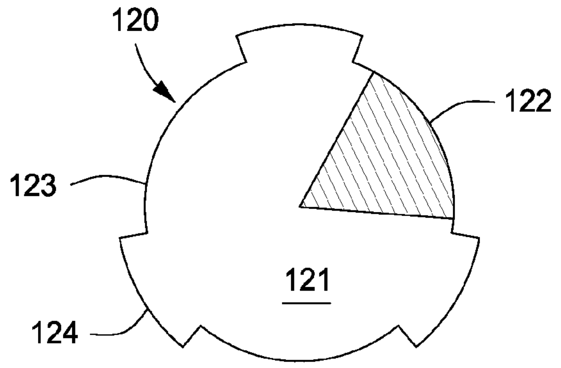
FIG. 9 is an orthographic view from the top illustrating one exemplary embodiment of a dial lens of an illuminated display system, the dial lens includes at least one light filter.

FIG. 9 illustrates one exemplary embodiment of a dial lens 120 component of a base assembly. The dial lens 120 includes a lens body 123. In operation, the dial lens 120 is placed over a plurality of light emitters from a display interface. In one exemplary embodiment, lens tabs 124 extend outwardly from the lens body to facilitate attachment to a dial assembly.

For the embodiment shown in FIG. 9, the dial lens 120 includes a cover portion 121 and a passageway portion 122. The cover portion 121 is characteristically opaque to prevent the diffusion of light from the display interface through the cover portion 121. The passageway portion 122 characteristically permits light diffusion from the display interface through the passageway portion 122. In one exemplary embodiment, the passageway portion 122 is transparent. In one exemplary embodiment, the passageway portion 122 is translucent.

The passageway portion 122 modifies light emission from the display interface in a predetermined manner by which to send information relating to the status of a user. In one exemplary embodiment, the passageway portion 122 includes at least one light filter.

Illustratively, the passageway portion 122 of a dial lens 120 may be placed over the light emitters of FIG. 8 or FIG. 5 whereas the cover portion 121 may block light emission from other regions the respective base assembly. Moreover, in one exemplary embodiment, the passageway portion 122 may provide at least one light filter to modify light emission from the light emitter 117 of FIG. 8.

Figure 10:
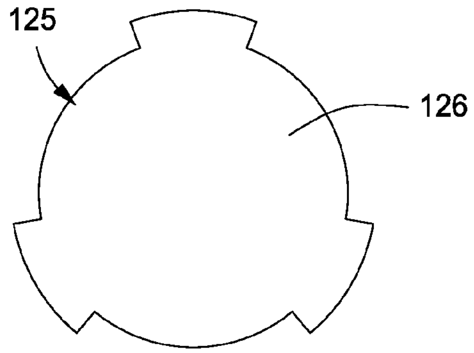
FIG. 10 is an orthographic view from the top illustrating one exemplary embodiment of a dial lens of an illuminated display system, the dial lens includes at least one light filter.

FIG. 10 illustrates one exemplary embodiment of a dial lens 125. The dial lens 125 includes a lens body 126 for operative engagement with a display interface of a base assembly. The dial lens 125 provides for light transmission therethrough. The dial lens 125 in one exemplary embodiment includes a light filter for uniformly modifying light transmitted through the entire dial lens 125.

Figure 11:
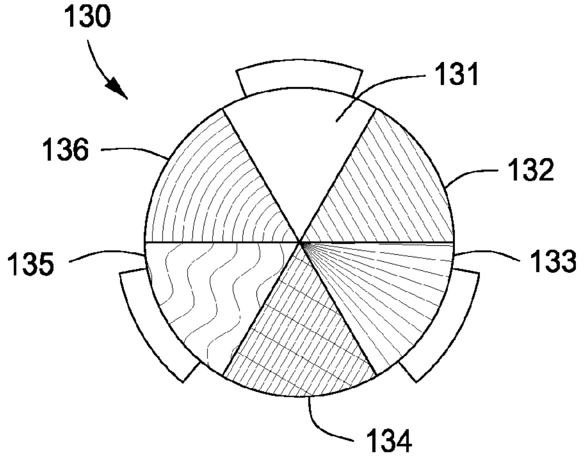
FIG. 11 is an orthographic view from the top illustrating one exemplary embodiment of a dial lens of an illuminated display system, the dial lens including a plurality of light filters.

FIG. 11 illustrates one exemplary embodiment of a dial lens 130. As shown, the dial lens 130 includes a plurality of light passageway portions. Each passageway portion uniquely modifies the light transmission therethrough with respect to the other passageway portions from the plurality of passageway portions.

In one exemplary embodiment, as shown in FIG. 11, dial lens 130 includes a cover portion 131. The cover portion 131 is characteristically opaque for preventing light transmission therethrough. Operatively, for example, the cover portion 131 of the dial lens 130 may be applied to the single light emitter 117 of the base assembly 115 of FIG. 8 to prevent the emission the white light therethrough.

The dial lens 130 of FIG. 11 further includes a plurality of passageway portions. In operation, a dial assembly selectively rotates the dial lens 130. Accordingly, the plurality of passageway portions provided by the dial lens 130 discretely modifies light emission from the light emitter 117.

Specifically, the dial lens 130 includes a first passageway 132. The first passageway 132 features a filter for generating infrared light emission. A second passageway 133 includes a filter for creating intermittent infrared light emission. A third passageway 134 features a filter for generating red visible light emission. A fourth passageway 135 includes a filter for creating green visible light emission. A fifth passageway 136 includes a filter for generating a blue visible light emission. Those of ordinary skill in the art will readily recognize the inclusion of other passageway portions for filtering light through the dial lens 130.

Figure 12:
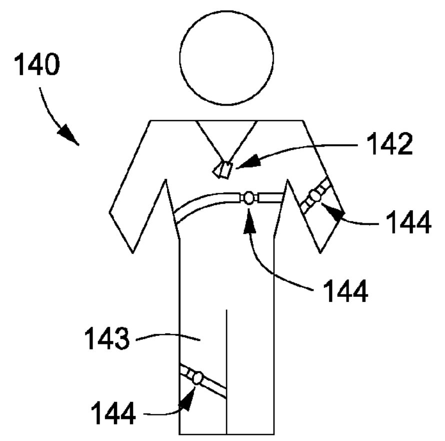
FIG. 12 is schematic diagram illustrating one exemplary embodiment of an illuminated display system in operative engagement with an injured soldier, the illuminated display system includes a plurality of light emitters, each light emitters for selective use to prioritize the degree of medical care administered to the injured soldier.

FIG. 12 shows at least one illuminated display system 144 in operative engagement with an injured user 140 such as an injured soldier. Accordingly, an illuminated display system 144 includes a plurality of light emitters whereby each light emitter emits a predetermined light signal used to prioritize the degree of care required by the injured user 140.

The illuminated display system 144 as shown in FIG. 12 is strapped on to the injured user 140. Illustratively, the illuminated display system 144 may be attached to the chest, arm, leg, neck, and head of a soldier or a soldier's equipment such as a backpack or gun. In one exemplary embodiment, the illuminated display system may be magnetically attached to the injured user's 140 clothing in a manner similar to that shown in FIG. 2. Specifically, clothing of the injured user, such as a hospital gown, military uniform or clothing worn during a disaster relief effort, may define a receiving element for facilitating affixation of an illuminated display system via a system of rare earth permanent magnets.

Consider the following battlefield scenario for illustrating how an illuminated display system 144 is applied to an injured user in the context of administering medical care to an injured soldier. A brief clinical assessment is first administered to the injured user 140 to prioritize the degree of medical care required relative to others that are injured on the battlefield. The illuminated display system 144 is then secured to the injured user 140.

The illuminated display system 144 specifically includes a base assembly. The base assembly includes a base body having a top portion and a bottom portion. The base assembly further includes a display interface disposed on the top portion of the base body. The display interface includes a plurality of light emitters. Each light emitter from the plurality of light emitters provides a predetermined wavelength of light than the other light emitters from the plurality of light emitters. The illuminated display system further includes a dial assembly operatively coupled to the base assembly. The dial assembly includes a dial lens positioned above the display interface. The illuminated display system further includes a selector for electrically activating desired light emitter from the plurality of light emitters.

Once the illuminated display system 144 is secured to the injured user 140, the dial assembly is adjusted relative to the display interface. Accordingly, based on medical information gathered from the brief clinical assessment, the selector is moved adjacent to a desired light emitter. The desired light emitter is activated via a voltage signal provided by the selector. The desired light emitter is illuminated at a characteristic predetermined wavelength of light that provides information relating to the degree or nature of injury sustained by a soldier in the form of a light signal. Accordingly, the plurality of light emitters provides a menu of light signals that correspond to the medical condition of each particular injured user 140 in a triage situation. Selecting a desired light emitter on the illuminated display system 144 is quick and easy, especially when conditions are too dangerous to provide immediate care. In one exemplary embodiment, the light signals are based on predetermined information. In one exemplary embodiment, the light signals are based a color scheme of a type well know in medical triage.

The desired light emitter may remain illuminated for several hours to allow medical care to be prioritized relative to other injured soldiers, especially in determining transport and treatment priorities. Moreover, the desired light emitter may remain illuminated in several low-visibility settings such as in complete darkness, in smoke, fog or dust, episodes of adverse weather such as snow or rain or in areas of dense undergrowth, snow cover, or while submerged. It should be added that the injured user 140 in FIG. 12 is also wearing information tags such as military "dog tags" for providing additional information or information provided by military "dog tags" may be disposed on an illuminated display system.

In a further illustration, consider the following scenario for displaying information on a user. An illuminated display system 144 is secured to the user. Accordingly, the user identifies information to be conveyed by the illuminated display system 144 based on a predetermined menu provided by the illuminated display system 144. For example, in one exemplary embodiment, a predetermined menu may best reflect the basic needs of the user at any given time for a variety of situations such as, among others, if the user needs medical assistance, transportation assistance, shelter, food and water or directional assistance. As such, the dial assembly of the illuminated display system 144 is adjusted relative to the display interface so that the selector is positioned adjacent to the desired light emitter from the dial assembly. The selector applies a voltage across the desired light emitter for activation thereof. The light emitter is thus illuminated at a desired, predetermined wavelength representing the corresponding predetermined status of the user.

Figure 13:
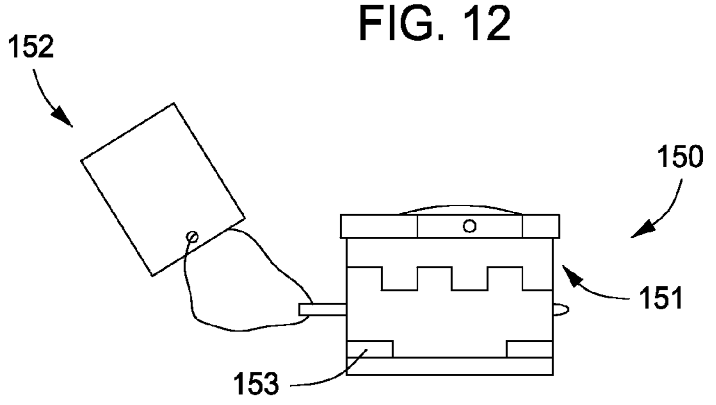
FIG. 13 is schematic diagram illustrating one exemplary embodiment of an illuminated display system in operative engagement with an information card, such as triage data card.

FIG. 13 illustrates one exemplary embodiment of a military information display system 150. The military information display system 150 includes an illuminated display system 151 and a triage data card 152 coupled to the illuminated display system 151. The illuminated display system 151 is similar to those embodiments, among others, shown in FIGS. 1-12 as well as succeeding embodiments shown in FIGS. 15, 19, 20, and 21-27. The illuminated display system 151 includes a fastening interface 153. The fastening interface 153 may be operatively coupled to the uniform of an injured solider so that the illuminated display system 151 may emit light signals on the outside of the soldier's uniform while remaining secured to the uniform. The triage data card 152 may also include information relating to the injured soldier.

Figure 14:
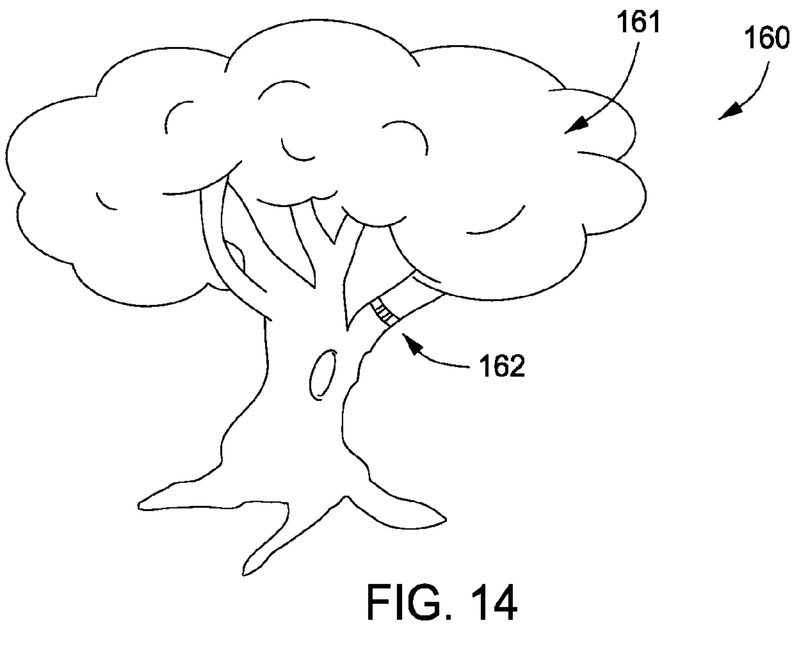
FIG. 14 is schematic diagram illustrating one exemplary embodiment of an illuminated display system in operative engagement with a receiving element, such as a tree, the illuminated display system including a plurality of light emitters each light emitter providing information such as geographical information.

FIG. 14 illustrates one exemplary embodiment of a geographical information display system 160. The geographical information display system 160 includes a receiving element 161 and an illuminated display system 162 coupled to the receiving element 161. As shown, the receiving element 161 comprises a tree. However, the receiving element 161 may comprise any geographical marker of a type well known in industry such as in scouting, warfare tactics, and survival tactics.

Operatively, the illuminated display system 160 is coupled to the receiving element 161. The illuminated display system 160 provides a light signal corresponding to predetermined information such as directional location, environmental conditional status or other conditional status.

Figure 15:
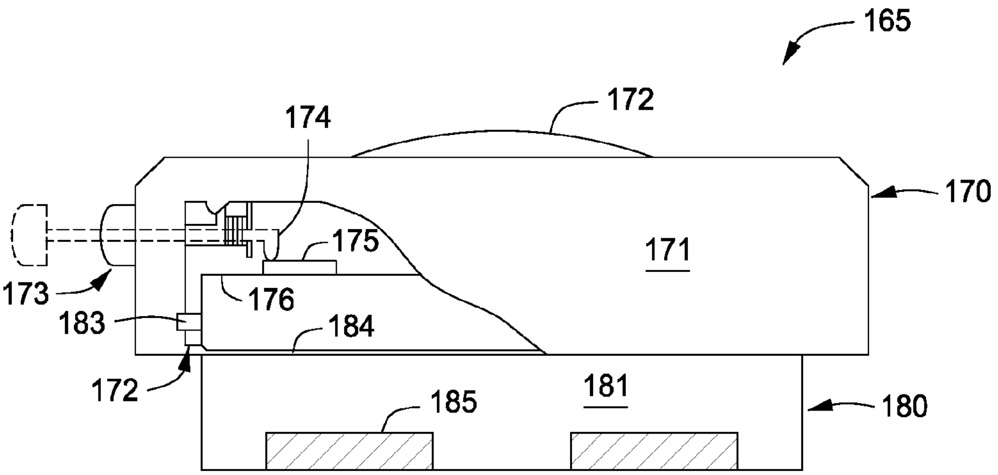
FIG. 15 is a cut-away orthographic view from the side illustrating one exemplary embodiment of an illuminated display system, the illuminated display system including a selector, the selector for electrically switching a desired light emitter from a plurality of light emitters provided by the illuminated display system.

FIG. 15 illustrates one exemplary embodiment of an illuminated display system 165. In particular, FIG. 15 shows a cut-away view of an area surrounding a selector 173. In use, the selector 173 electrically engages a desired light emitter from a plurality of light emitters.

The illuminated display system 165 includes a dial assembly 170. The dial assembly 170 includes a dial body 171. A dial lens 172 is provided on the dial body 171. Operatively, the dial lens 172 facilitates viewing of at least one light emitter from the plurality of light emitters.

The illuminated display system 165 further includes a base assembly 180 operatively coupled to the dial assembly 170. The base assembly 180 includes a base body 181. The base body 181 features a top portion and a bottom portion. As such, a fastening interface 85 is provided at the bottom portion of the base body 181. A display interface 176 is positioned on the top portion of the base body 181.

The display interface 176 includes a plurality of light emitters. The plurality of light emitters may be arranged in a variety of configurations such as arrangements shown in FIGS. 4-8. The display interface 176 includes a series of contact terminal units 175 whereby each contact terminal unit 175 is positioned adjacent to a corresponding light emitter from the plurality of light emitters for electrical activation thereof.

As shown in the embodiment of FIG. 15, a spring and cam arrangement is provided to extend and retract the selector 173 relative to a desired contact terminal unit 175. Specifically, FIG. 15 shows the selector 173 in an extended position. In the extended position, the selector 173 cooperates with a contact bridge 174 to form a closed electrical circuit at the respective contact terminal unit 175. The closed circuit ultimately supplies a voltage to a corresponding desired light emitter adjacent to the contact terminal unit 175. The voltage applied to the desired light emitter ultimately provides information relating to a user's status. Alternatively, via the cam and spring arrangement, the selector 173 may be rendered in a retracted position to disengage the contact bridge 174 from the terminal unit 175 to form an open electrical circuit.

The dial assembly 170 of FIG. 15 rotates about the display interface 176 to position the selector 173 adjacent to a contact terminal unit for operating a desired light emitter. Specifically, the base body 181 defines an interface groove 184. The interface groove 184 receives an interface notch 172 defined by the dial body 171 so as to secure the dial assembly 170 to the base assembly 180 and thus facilitate rotational movement about the interface groove 184.

FIG. 15 further illustrates a locator tooth 183 in contact with the dial body 171. As previously discussed, the locator tooth 183 may provide information about the positioning of the dial assembly 170, specifically the selector 173, with respect to the base assembly 180 by means of touch and, optionally, of sound without visual confirmation. Accordingly, the locator tooth 183 of FIG. 15 is similar to the locator teeth shown in FIGS. 4-8.

Figure 16:
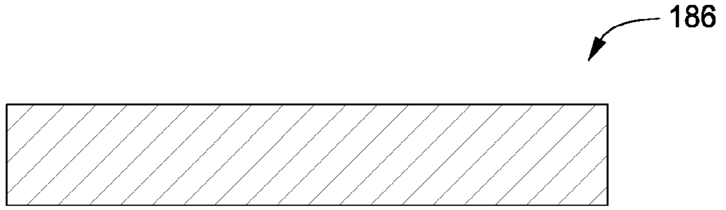
FIG. 16 is an orthographic view from the side illustrating one exemplary embodiment of a clamp member for engagement with a fastening interface of an illuminated display system.

FIG. 16 illustrates one exemplary embodiment of a clamp member 186. Accordingly, the clamp member 186 may be operatively coupled to the fastening interface 185 of the illuminated display system 165 of FIG. 15. In one exemplary embodiment, the clamp member 186 may be composed of a magnetically attractive material such as iron. In one exemplary embodiment, the clamp member 186 comprises a permanent magnet such as a rare earth permanent magnet.

Figure 17:
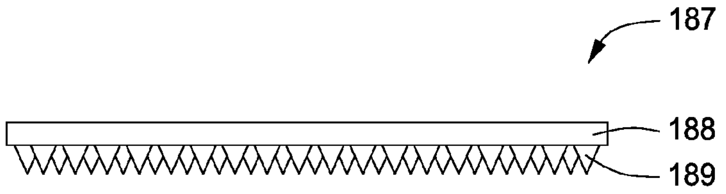
FIG. 17 is an orthographic view from the side illustrating one exemplary embodiment of a clamp member for engagement with a fastening interface of an illuminated display system.

FIG. 17 illustrates one exemplary embodiment of a clamp member 187. The clamp member 187 may be operatively coupled to the illuminated display system 165 of FIG. 15. The clamp member 187 includes a substrate 188 and a forked array 189 disposed on the substrate 188. The substrate 188 may be composed of a magnetically attractive material such as iron or a permanent magnet to facilitate attachment to the fastening interface 185 of the illuminated display system 165. The forked array 189 is configured to be driven into a receiving object so as to ultimately secure the illuminated display system 165 of FIG. 15 to the receiving object.

Figure 18:
FIG. 18 is an orthographic view from the side illustrating one exemplary embodiment of a clamp member for engagement with a fastening interface of an illuminated display system.

FIG. 18 illustrates one exemplary embodiment of a clamp member 190. The clamp member 190 includes a substrate 191 and an adhesive member 192 disposed on the substrate 191.

The adhesive member 192 attaches to a user or receiving object and thus secures the illuminated display system 165 to a user or receiving object. The adhesive member 192 may be composed of any adhesive material of a type well known in the industry such as glue, gum or VELCRO.

In one exemplary embodiment, the substrate 191 is composed of a magnetically attractive material such as iron or a permanent magnet. In operation, the substrate 191 is secured to the fastening interface 185 supplied by the illuminated display system 165 of FIG. 15.

Figure 19:
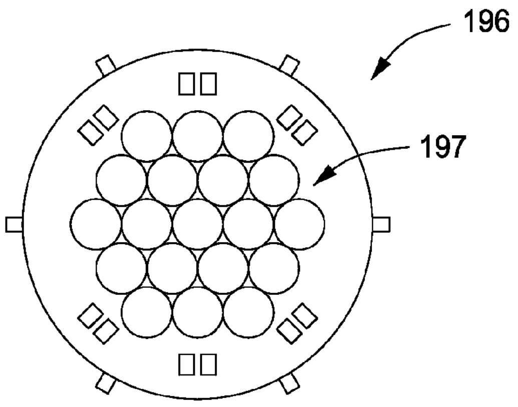
FIG. 19 is an orthographic view from the top illustrating one exemplary embodiment of a base assembly of an illuminated display system, the base assembly including a variable intensity emitter array.

FIG. 19 illustrates one exemplary embodiment of a base assembly 196 for an illuminated display system. The base assembly 196 includes a plurality of light emitters defining a variable intensity emitter array 197.

The variable intensity emitter array 197 is operatively coupled to a control system (not shown). In one exemplary embodiment, the control system adjusts the intensity of light produced by at least one light emitter from the variable intensity emitter array 197. In effect, the control system applies a variable resistance to the variable intensity emitter array 197 to selectively dim the brightness level of light emission from the variable intensity emitter array 197. Moreover, in one exemplary embodiment, the control system may adjust the duration of light signal produced by at least one light emitter from the variable intensity emitter array 197. In particular, the control system applies a timer sequence to adjust the duration of light signal produced.

Figure 20:
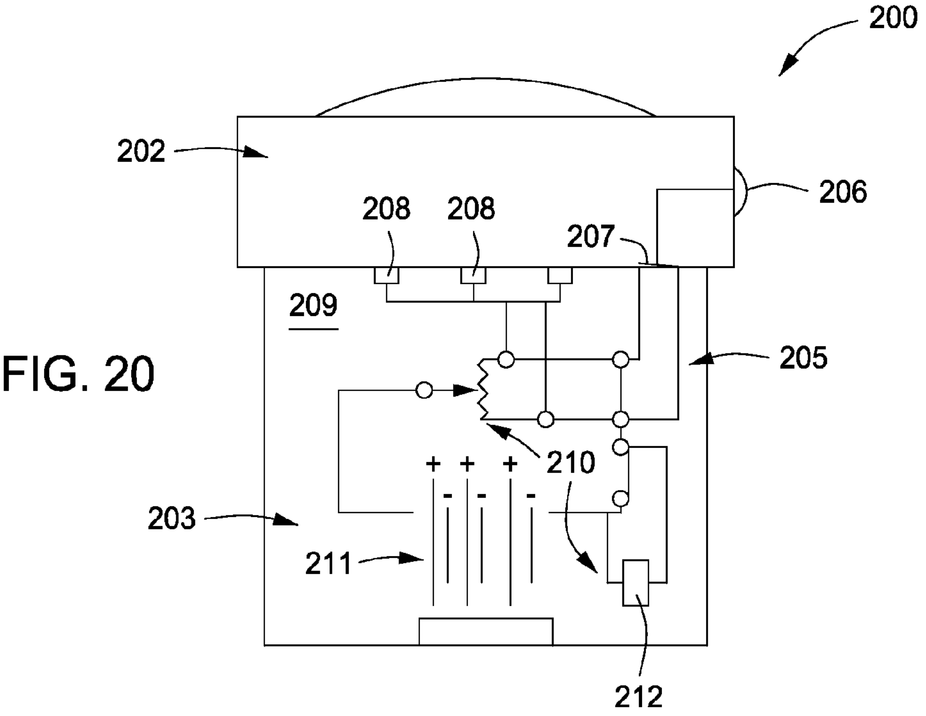
FIG. 20 is schematic view from the side illustrating one exemplary embodiment of an illuminated display system, the illuminated display system featuring a variable intensity assembly.

FIG. 20 illustrates one exemplary embodiment of an illuminated display system 200 featuring a variable intensity assembly 205. As shown from the side, the illuminated display system 200 of FIG. 20 includes a dial assembly 202 and a base assembly 203 coupled with the dial assembly 202. For the embodiment of FIG. 20, the base assembly 203 includes a base body 209 relatively larger in size than the dial assembly 202. Accordingly, the base body 209 is sufficiently large enough to accommodate a large power supply 211 such as an array of batteries.

Furthermore, a selector contact interface 207 is disposed on the base body 209. Operatively, a selector 206 coupled to the dial assembly 202 closes a circuit at the selector contact interface 207 to activate the variable intensity assembly 205.

The variable intensity assembly 205 includes a control system 210. As shown in FIG. 20, the control system 210 is electrically coupled to a plurality of light emitters 207. Operatively, in one exemplary embodiment, the control system 210 adjusts the intensity of light produced by at least one light emitter from the plurality of light emitters 208. In particular, the control system 210 includes a microprocessor 212 coupled to a variable resistor for selectively dimming the voltage applied to the plurality of light emitters 208. In one exemplary embodiment, the control system 210 is electrically coupled with the selector 206 to operatively dim the plurality of light emitters.

Illustratively, the selector 206 may comprise a spring-loaded button whereby a first depression of the button would permit a corresponding light emitter to provide the brightest level of light, two sequential depressions of the button providing a medium light level, and three sequential depressions providing the lowest light level. Those of ordinary skill in the art will readily recognize other dimming arrangements of the plurality of light emitters via a control system.

In one exemplary embodiment, the control system 210 adjusts the duration of light signal produced by at least one light emitter from the plurality of light emitters 208. Specifically, the control system 210 features a microprocessor that includes a timer sequence for opening and closing a relay.

Figure 21:
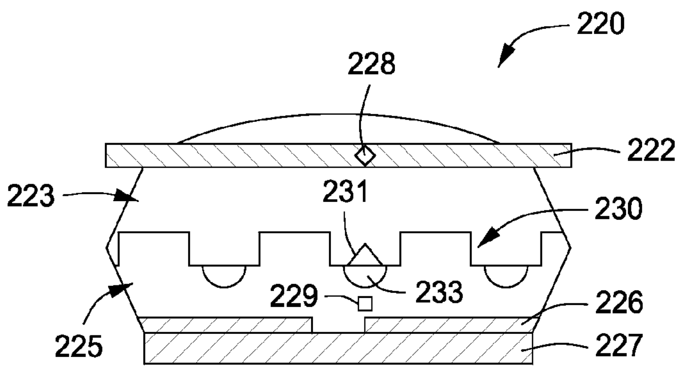
FIG. 21 is an orthographic view from the side illustrating one exemplary embodiment of an illuminated display system, the illuminated display system featuring an interlocking assembly for selectively activating a desired light emitter from a plurality of light emitters.

FIG. 21 illustrates one exemplary embodiment of an illuminated display system 220. The illuminated display system 220 includes a dial assembly 223 and a base assembly 225. In operation, the dial assembly 223 and the base assembly 225 cooperate to define an interlocking assembly 230. Accordingly, a desired light emitter from a plurality of light emitters may be selectively activated by first separating the dial assembly 223 from the base assembly 225, aligning the interlocking assembly 230 according to the position of the desired light emitter, and then recombining the dial assembly 223 with the base assembly 225. The dial assembly 223 and the base assembly 225, in one exemplary embodiment, are held together by magnetic attraction along the interlocking assembly 230. Specifically, the dial assembly 223 and the base assembly 223 may be composed, at least in part, of a magnetically attractive material.

As shown in FIG. 21, the base assembly 225 includes a series of contact terminals 233. The contact terminals 233 are electrically coupled to corresponding light emitters from the plurality of light emitters. A selector 228 is provided on the dial assembly 223 to electrically activate a desired light emitter from the plurality of light emitters. As shown in FIG. 21, the selector 228 cooperates with a contact bridge 231 to electrically close a circuit formed at a desired contact terminal 233. The closed circuit formed by the contact bridge 231 and the contact terminal 233 electrically activates a corresponding light emitter.

Each contact terminal 233 corresponds to a light emitter from the plurality of light emitters whereby each light emitter radiates a different predetermined wavelength of light than the other light emitters. Accordingly, a unique predetermined wavelength of light may be selected from the plurality of light emitters for providing corresponding information relating to particular user's status.

In one exemplary embodiment, the interlocking assembly 230 is held together by magnetic attraction. In particular, the dial assembly includes a lens guard 222. The lens guard 222 is composed of a magnetically attractive material such as iron or a permanent magnet. Similarly, the base assembly 225 includes a fastening interface 226. The fastening interface 226 is composed of a magnetic material that is attracted to the lens guard 222. Ultimately, the magnetic attraction between the lens guard 222 and fastening interface secures the interlocking assembly 230 in place.

In one exemplary embodiment, a clamp member 227 may be comprised of a magnetically attractive material. In effect, the clamp member 227 further enhances the magnetic attraction between the dial assembly 223 and the base assembly 225.

Moreover, as shown in FIG. 21, the base assembly 225 includes an alignment node 229 extending outwardly from the base assembly 225. In operation, the alignment node 229 aids in identifying the orientation of each light emitter from the plurality of light emitters by touch alone without visual confirmation. Accordingly, because both the alignment node 229 and the plurality of light emitters are each at a fixed location on the base assembly 225, the location of at least one light emitter can be identified without visual confirmation relative to the alignment node 229 shown in FIG. 26.

Figure 22:
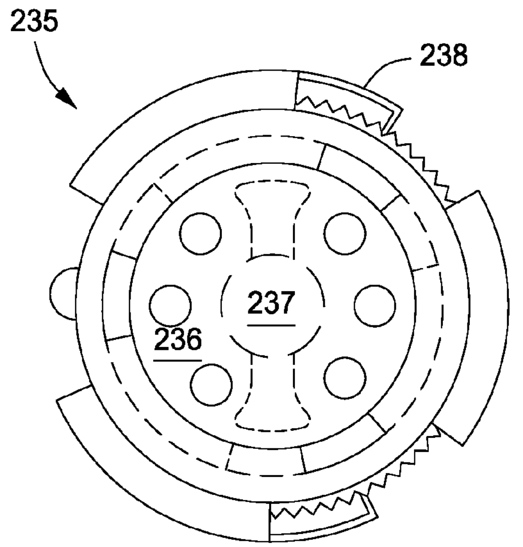
FIG. 22 is an orthographic view from the top illustrating one exemplary embodiment of an illuminated display system, the illuminated display system features a receiving chamber.

FIG. 22 is a top view of a top view illustrating one exemplary embodiment of an illuminated display system 235. The illuminated display system 235 includes a base assembly 236. As shown in phantom in FIG. 22, the base assembly 236 defines a receiving chamber 237. The receiving chamber 237 is configured to accommodate a wide range of useful items such as biomedical sensors like heart-rate monitors and other well known sensors, radio frequency (RF) identification microprocessors, global positioning system (GPS) locators and other well known locators, memory storage devices, transmitters, and additional batteries. As shown in FIG. 22, the illuminated display system 235 further includes a fastening interface 238. In particular, the fastening interface 238 includes at least one securing loop. The at least one securing loop extends outwardly from the base assembly 236.

Figure 23:
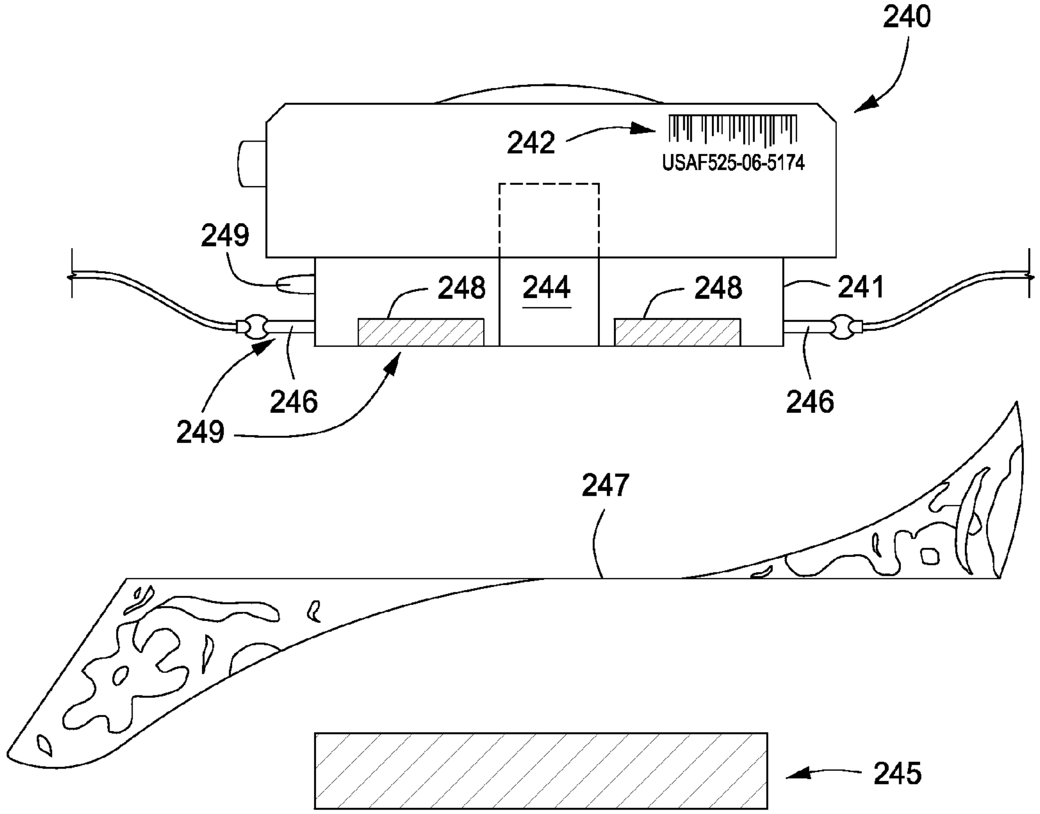
FIG. 23 is an exploded view from the side illustrating one exemplary embodiment of an illuminated display system in engagement with a receiving element such as a military uniform, the illuminated display system includes a receiving chamber, a fastening interface, and a clamp member whereby the receiving element is operatively fixed between the fastening interface and the clamp member.

FIG. 23 illustrates one exemplary embodiment of an illuminated display system 240 in engagement with a receiving object 247. Illustratively, the receiving object 247 comprises a soldier's military uniform. The illuminated display system 240 further includes a military information label 242 that includes information specific to an individual soldier such as an issue number, birth date, and other information found on a military "dog tag".

The illuminated display system 240 includes a base body 241. The base body 241 of FIG. 23 defines a receiving chamber 244. The base body 241 further includes a fastening interface 243. As shown in FIG. 23, the fastening interface 243 includes at least one securing loop 246 extending outwardly from the base assembly 241. In operation, straps may be tied to the at least one securing loop 246 so that, ultimately, the illuminated display system 240 may be strapped onto a receiving object. Moreover, as shown in FIG. 23, the fastening interface 243 includes a magnetic member 248 for operative engagement with a clamp member 245.

Figure 24:
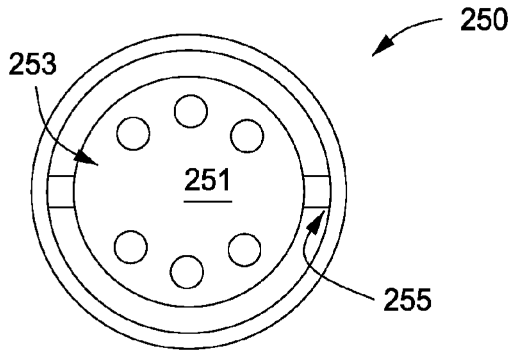
FIG. 24 is an orthographic view from the top illustrating one exemplary embodiment of an illuminated display system, the illuminated display system featuring a fastening interface.

FIG. 24 illustrates one exemplary embodiment of an illuminated display system 250. The illuminated display system 250 includes a base body 251. Accordingly, a display interface 253 is disposed on the base body 251.

The illuminated display system 250 further includes a fastening interface 255. Operatively, the fastening interface 255 receives at least one securing strap for fixating the position if the illuminated display system 250. As shown in FIG. 24, the fastening interface 255 comprises at least one securing loop extending outwardly from the base assembly.

Figure 25:
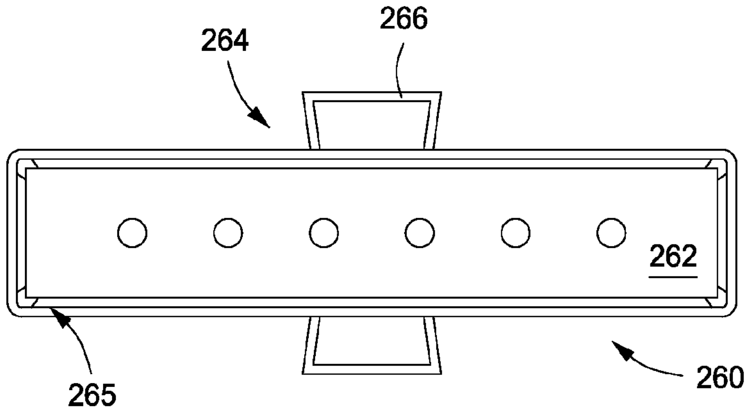
FIG. 25 is an orthographic view from the top illustrating one exemplary embodiment of an illuminated display system, the illuminated system includes a first loop assembly and a second loop assembly.

FIG. 25 is a top view illustrating one exemplary embodiment of an illuminated display system 260. The illuminated display system 260 includes a base body 262.

Furthermore, the illuminated display system 260 includes a fastening interface 264. Operatively, the fastening interface 264 facilitates securing of the illuminated display system 260 on to a user or a receiving object. The illuminated display system 260 may be activated either in a manner similar to that described of FIGS. 1-24 or by any suitable means well known in the industry. As shown in FIG. 25, the fastening interface 264 includes a first securing loop assembly 265 and a second securing loop assembly 266, each extending outwardly from the base body 262. The first securing loop assembly 265 and the second securing loop assembly 266 are provided to receive several securing straps of different sizes and applied at different angles.

Figure 26:
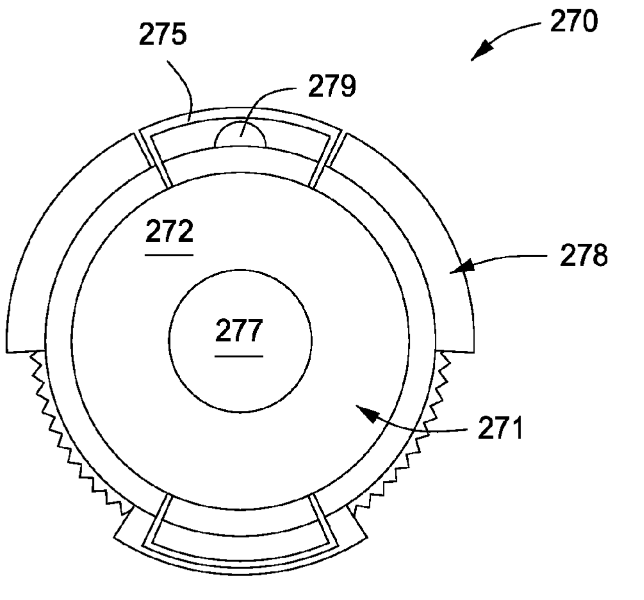
FIG. 26 is an orthographic view from the bottom illustrating one exemplary embodiment of an illuminated display system, the illuminated display system includes at least one fastening interface aligned relative to a selector.

FIG. 26 is a bottom view illustrating one exemplary embodiment of an illuminated display system 270. The illuminated display system 270 includes a base assembly 271 and a dial assembly 278 rotatably coupled to the base assembly 271. A selector 279 is disposed on the dial assembly 278 to ultimately activate a desired light emitter from a plurality of light emitters.

The illuminated display system 270 further includes a fastening interface 275. As shown in FIG. 26, the fastening interface 275 comprises at least one securing loop extending outwardly from the base assembly 271. Moreover, in one exemplary embodiment, the base assembly 271 provides a base body 272. As shown in FIG. 26, the fastening interface 275 is positioned on the base body 272 in a configuration that promotes readily identifying the location of the selector 279 relative to the fastening interface 275 without visual confirmation. Specifically, as shown in FIG. 26, the fastening interface 125 includes two opposing securing loops that are 180° apart from one another on the base assembly 271. Accordingly, because both the opposing securing loops and a plurality of light emitters are each at a fixed location on the base assembly 271, the location of the selector 279 may be identified without visual confirmation relative to the plurality of light emitters by referring to the opposing securing loops shown in FIG. 26.

The illuminated display system 240 further includes a sensor 277 disposed on the base body 272. In one exemplary embodiment, the sensor 277 may comprise a biosensor well known in the industry such as electrodes and pulse oximetry sensors. Accordingly, in operation, as the base body 272 engages against a user's body, the sensor 277 collects biologic information such as heart beat, pulse rate, and level of oxygen content within a blood stream. In one exemplary embodiment, the sensor 277 is operatively coupled to a plurality of light emitters from the illuminated display system 270 for illumination of the plurality of light emitters in response to data collected by the sensor 277.

Figure 27:
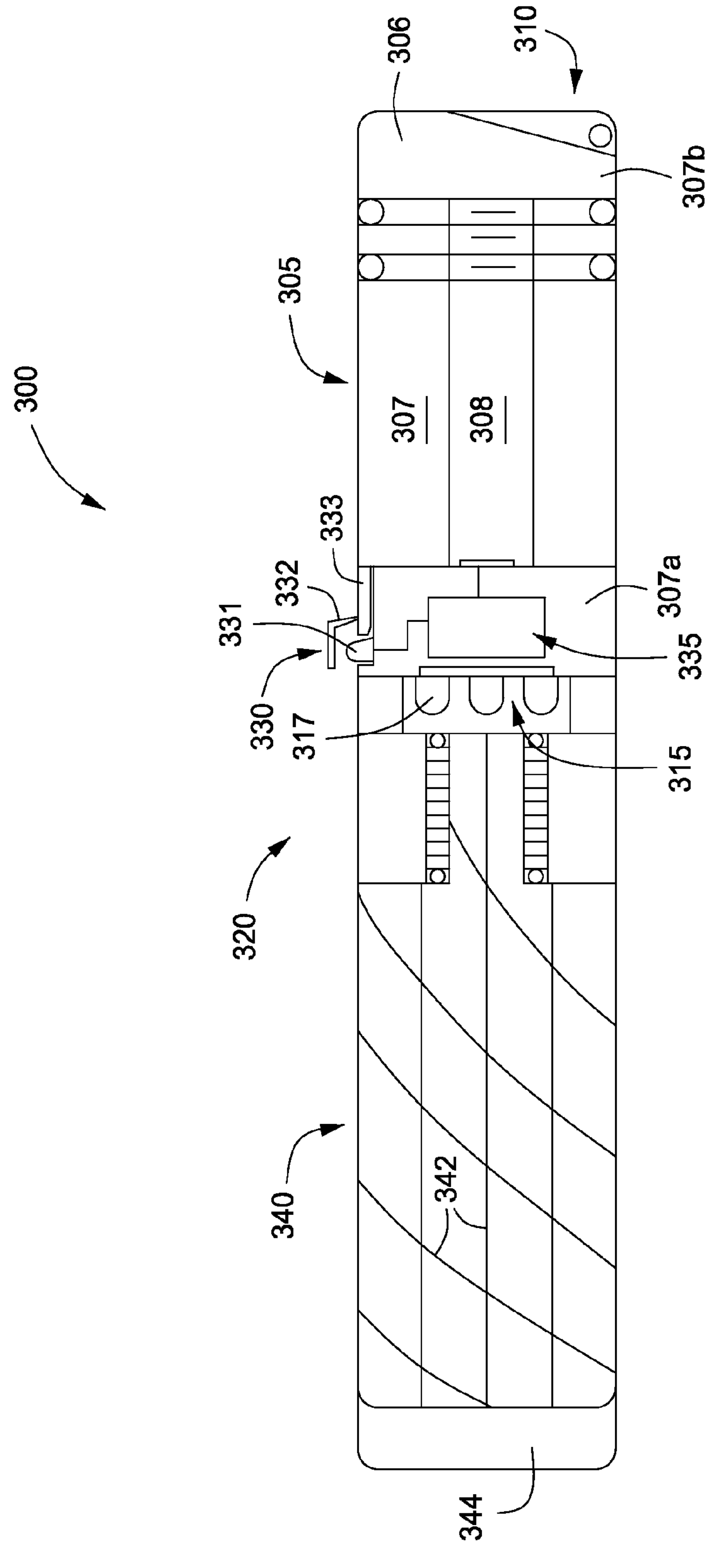
FIG. 27 is a schematic view from the side illustrating one exemplary embodiment of an illuminated display system, the illuminated display system includes a selector to activate a desired light emitter from a plurality of light emitters to ultimately emit light from a dial lens.

FIG. 27 illustrates one exemplary embodiment, among others, of an illuminated display system 300. In general, the illuminated display system 300 includes a dial lens 340 for facilitating light travel therethrough. In one exemplary embodiment, the dial lens 340 provides a direct path, an indirect path or combination thereof for light travel therethrough.

As shown in the exemplary embodiment of FIG. 27, the illuminated display system 300 includes a base assembly 305. The base assembly 305 includes a base body 307. In one exemplary embodiment, the base body 307 may be composed of a durable, light weight material such as, among others, a polymer, metal or metal alloy. In one exemplary embodiment, the base body 307 is composed of either a transparent or translucent material to facilitate light travel therethrough.

In one embodiment, the base body 307 defines at least one receiving chamber 308. The at least one receiving chamber 308 is configured to accommodate a wide range of useful items as recognized by those of ordinary skill in the art such as among others batteries for providing power to the illuminated display system 300, spare batteries, biomedical sensors like hart rate monitors as well as other well known sensors, radio frequency (RF) identification microprocessors, global positioning system (GPS) locators and other well known locators, memory storage devices, and transmitters.

As shown in FIG. 27, the base body 307 may be divided into a first portion 307*a* and a second portion 307*b*. Those of ordinary skill in the art will readily recognize that the base body 307 may be divided in any number of portions.

In one exemplary embodiment, the illuminated display system 300 further includes a fastening interface 310. The fastening interface 310 of FIG. 27 is positioned at the second portion 307*b* of the base body 307. The fastening interface 310 is operatively coupled to a user such as, among others, an injured soldier in battlefield settings.

For example, as shown in FIG. 27, the fastening interface 310 may define a bore for receiving a cord, pin or ring therethrough. In one exemplary embodiment, the fastening interface 310 includes a magnet such as, among others, a rare earth permanent magnet.

In one exemplary embodiment, the second portion 307*b* of FIG. 27 defines a cap 306 that is operatively removable from the base assembly 305. The cap 306 provides access to the at least one receiving chamber 308 denied by the base body 307. In one exemplary embodiment, at least one hermitic seal is provided between the cap 306 and the remaining base body 307 for receiving the cap 306. For example, at least one "O-ring" seal is operatively engaged with the attached cap 306 to provide a waterproof, hermetic seal as applied to the at least one receiving chamber 308. In one exemplary embodiment, the "O-ring" seal may operate at a depth of up to one hundred feet of seawater.

The illuminated display system 300 further includes a display interface 315. As shown in the embodiment of FIG. 27, the display interface 315 is disposed on the first portion 307*a* of the base body 307. The display interface 315 includes a plurality of light emitters 317. At least one light emitter from the plurality of light emitters is selected for illumination thereof according to the injury of the user. Each light emitter from the plurality of light emitters 317 provides a different, predetermined wavelength of light than the other light emitters from the plurality of light emitters 317. In effect, each respective wavelength provides information such as, among others, predetermined information. Illustratively, among others, this predetermined information includes information relating to the degree of injury of the injured user with respect to a plurality of injured users, the degree of injury of a soldier in battlefield settings, and information relating to a corresponding predetermined status of the user.

It should be added that in one exemplary embodiment, the plurality of light emitters 317 includes a light emitting diode. In one exemplary embodiment, the light emitting diode comprises an organic light emitting diode. In one exemplary embodiment, the light emitting diode provides an infrared wavelength band of light. In one exemplary embodiment, the light emitting diode intermittently provides an infrared wavelength band of light. In one exemplary embodiment, the light emitting diode provides a red visible light wavelength band. In one exemplary embodiment, the light emitting diode provides a blue visible light wavelength band. In one exemplary embodiment, the light emitting diode provides a green visible light wavelength band.

While operatively illuminated, the illuminated display system 300 is attached to the user or receiving object. Illustratively, in one exemplary embodiment, illumination of a desired light emitter provides information describing the current status of the user such as, among others, the kind of injury received, the likelihood for injury recovery, and the location of the injured party.

The illuminated display system 300 further includes a dial assembly 320. The dial assembly 320 is operatively coupled to the base assembly 305. In general, the dial assembly 320 includes a selector 330 and a dial lens 340.

The selector 330 is operatively coupled to the plurality of light emitters 317. As shown in the embodiment of FIG. 27, the illuminated display system 300 further includes a control system 335. The control system 335 is coupled to the plurality of light emitters 317. In one exemplary embodiment, in conjunction with the control system 335, the selector 330 is manipulated to either electrically engage or disengage a desired light emitter from the plurality of light emitters 317.

Generally, in one exemplary embodiment, the illuminated display system 300 is rendered in a continuous, electrically "off" position until the selector 330 engages a desired light emitter from the plurality of light emitters 317. In this manner, the illuminated display system 330 is illuminated as desired.

Generally, in operation, the selector 330 electrically activates a desired light emitter from the plurality of light emitters 317. The selector 330 applies a voltage to the desired light emitter for illumination thereof. Accordingly, illumination of the desired light emitter may signify information relating to a predetermined status of a user such as for example, the degree of injury of a soldier in battlefield settings or degree of injury of an injured user with respect to a plurality of injured users.

It should be added that those of ordinary skill in the art will readily recognize that the selector 330 may comprise any type of electrical interface of a type well known in the industry, such as, among others a switch, a button, a toggle switch, and a keypad. Moreover, it should be added that those of ordinary skill in the art will readily recognize that the control system 335 may comprise any suitable control system of a type well known in the industry such as, among others, a microprocessor-based control system. In operation, the control system 335 facilitates selective, electrical engagement of at least one light emitter from the plurality of light emitters 317 via the selector 330. Illustratively, the control system 335 may feature at least one predetermined illumination sequence with respect to the plurality of light emitters 317.

Generally, for example, consider the following predetermined illumination sequence as activated by depressing a selector coupled to the control system 335. Initially, the plurality of light emitters is rendered in an electrically "off" position. Thus, depressing the selector coupled to the control system 335 once activates an infrared light emitter from the plurality of light emitters. A second sequential depression of the selector would permit the infrared light emitter to illuminate intermittently or "blink". A third sequential depression of the selector would only activate a light emitter in the red visible light wavelength band. A fourth sequential depression of the selector would only activate a light emitter in the blue visible light wavelength band. A fifth sequential depression of the selector would only activate a light emitter in the green visible light wavelength band. A sixth sequential depression of the selector renders the entire plurality of light emitters in the electrically "off" position. Moreover, at any time during the above sequence, holding down the selector continuously for a predetermined period, such as for example two seconds, would completely start over the sequence beginning with the "off" position.

In one exemplary embodiment, the control system 335 adjusts the intensity of light produced by at least one light emitter from the plurality of light emitters 317. In effect, the control system 335 applies a variable electrical resistance to selectively dim the brightness level of light emission from the at least one light emitter of the plurality of light emitters 317.

In one exemplary embodiment, the control system 335 adjusts the duration of light signal produced by at least one light emitter from the plurality of light emitters 317. Accordingly, the control system 335 applies an electrical timer sequence to adjust the duration of light signal produced.

Referring specifically the embodiment of the selector 330 as shown in FIG. 27, the selector 330 includes a mode activation button 331. Particularly, a desired light emitter from the plurality of light emitters 317 is selected through a series of sequential depressions against the mode activation button 331 to electrically engage the desired light emitter. In effect, depressing the mode activation button 331 electrically closes a circuit for selectively engaging a desired light emitter from the plurality of light emitters 317.

The selector 330 for the embodiment of FIG. 27 further includes a button cover 332. Operatively, the button cover 332 shields the mode activation button 331 from inadvertent depression and thus activation of at least one light emitter from the plurality of light emitters 317.

Optionally, as shown in FIG. 27, the selector 330 further includes a cover retraction system 333. In general, the cover retraction system 333 selectively permits exposure of the mode activation button 331 with respect to the button cover 333. The cover retraction system 333 for the embodiment of FIG. 27 either slideably retracts the button cover 332 to expose the mode activation button 331 or advances the button cover 332 to protect the button 331 from activating at least one light emitter from the plurality of light emitters 317.

Referring specifically the embodiment of the dial lens 340 as shown in FIG. 27, the dial lens 340 of the dial assembly 320 is positioned adjacent to the display interface 315. The dial lens 340 is secured to the base body 307, such as, among others, threadedly secured to the base body 307. In one exemplary embodiment, the dial lens 340 is releasably secured to the base body 307. Those of ordinary skill will readily recognize that the dial lens 340 and the base body 307 may be formed of one contiguous piece.

In one exemplary embodiment, a hermitic seal is established between the dial lens 340 and the base body 307. For example, as shown in FIG. 27, a plurality of "O-ring" seals are placed in conjunction with the threaded joining of the dial lens 340 to the base body 307. In effect, the plurality of "O-ring" seals provide a waterproof, hermetic seal as the dial lens 340 is joined with the base assembly 305. In one exemplary embodiment, the plurality of "O-ring" seals may operate at a depth of up to one hundred feet of seawater.

In one exemplary embodiment, the dial lens 340 may be composed of one solid piece of material such as, among others, a polymer such as LUCITE, a ceramic or a metal. Those of ordinary skill in the art will readily recognize that the dial lens 340 may include a combination of elements that permit either direct or indirect transmission of light through the dial lens 340.

For example, in one exemplary embodiment the dial lens 340 may be composed of a transparent material to permit the direct transfer of light therethrough. In one exemplary embodiment, the dial lens 340 may be composed of a translucent material.

For the exemplary embodiment of FIG. 27, the dial lens 340 includes optical modifiers 342. In operation, as the light is transmitted through the dial lens 340, the optical modifiers 342, in whole or in part, change the direction of light travel.

Illustratively, in one exemplary embodiment, the optical modifiers 342 comprise a series of reflecting surfaces in operative engagement with the dial lens 340. As such, light travels from a desired light emitter of the plurality of light emitters 317, through the dial lens 340, and is reflected off the optical modifiers 342 at least once to ultimately enhance visibility of the light as it is transmitted from the dial lens 340 to the surrounding environment.

Illustratively, in one exemplary embodiment, the optical modifiers 342 include at least one diffuser in operative engagement with the dial lens 340. As such, light travels from a desired light emitter of the plurality of light emitters 317, through the dial lens 340, and is scattered out by the optical modifiers 342 at least once to ultimately enhance visibility of the light as it is transmitted from the dial lens 340 to the surrounding environment.

It should also be added that those of ordinary skill in the art will readily recognize that optical modifiers 342 may assume a variety of geometrical arrangements with respect to the dial lens 340 so as to enhance the overall emission of light from the dial lens 340 to the surrounding environment. Some examples of optical modifiers 342, among others, include grooves or notches formed into the dial lens 340, mirrored surfaces, and translucent surfaces for disbursing light to enhance overall visibility the dial lens 340.

In one exemplary embodiment, the dial lens 340 includes light filters 344. Operatively, the light filters 344 either amplify or attenuate the wavelength band of light emitted by a desired light emitter of the plurality of light emitters 317 as the light travels from the dial lens 340 to the surrounding environment. Illustratively, in one exemplary embodiment, the light filters 344 include at least one polarizer to attenuate the direction of light emission from the dial lens 340 to the surrounding environment.

It should be added that for at least one exemplary embodiment of FIG. 27, the illuminated display system 300 further includes a plurality of interchangeable dial lenses 340. The plurality of interchangeable dial lenses 340 are releasably coupled to the base body 307. In one exemplary embodiment, the plurality of interchangeable dial lenses 340 feature a combination of optical modifiers 342 and light filters 344 to enhance the overall transmission of light emitted from the dial lens 340 to the surrounding environment. In one exemplary embodiment, each dial lens 340 features a unique, predetermined combination of optical modifiers 342 and light filters 344 for interchangeable engagement with the base body 307 such that each interchangeable dial lens 340 optimally accommodates the specific needs of the user in a variety of visibility conditions. For example, among others, each dial lens from the plurality of interchangeable dial lenses 340 features a unique combination of optical modifiers 342 and light filters 344 for specific use by a soldier in desert, woodland, amphibious, nautical, jungle, mountainous, and polar battlefield visibility conditions.

Consider the following battlefield scenario for illustrating how the illuminated display system 300 is applied to an injured user in the context of administering medical care to an injured soldier. On encountering an injured soldier, a brief clinical assessment is administered to the injured soldier to prioritize the degree of medical care required relative to others that are injured on the battlefield. The illuminated display system 300 is secured to the injured soldier.

The illuminated display system 300 specifically includes the base assembly 305 featuring a base body 307 having a first portion 307*a* and the display interface 315 including a plurality of light emitters 317. Each light emitter from the plurality of light emitters 317 provides a different predetermined wavelength of light than the other emitters from the plurality of light emitters 317. In one exemplary embodiment, each respective predetermined wavelength provides information relating to the degree of injury of the soldier. In one exemplary embodiment, the respective predetermined wavelength provides predetermined information relating to the degree of injury of the soldier.

The illuminated display system 300 of FIG. 27 includes the elements discussed in detail above. Accordingly, the illuminated display system 300 includes the selector 330 to activate the desired light emitter from the plurality of light emitters 317. Once the illuminated display system 300 is secured to the injured soldier, the selector 330 applies a voltage to activate the desired light emitter from the plurality of light emitters 317. Accordingly, the light emitter is illuminated at the desired predetermined wavelength to provide information relating to the degree of injury of the soldier.

It should be said that the plurality of light emitters 317 provide an array of light signals corresponding to a predetermined menu relating to common medical conditions encountered by an injured soldier in a battlefield triage situation. In one exemplary embodiment, the light signals are based on a color scheme of a type well known in medical triage. With the control system 335 and selector 330, choosing a desired light emitter on the display interface 315 is quick and easy especially when conditions are too dangerous to provide immediate care.

The desired light emitter may remain illuminated for several hours to allow medical care to be prioritized relative to other injured soldiers, especially in determining transport and treatment priorities. Moreover, the desired light emitter may remain illuminated in several low-visibility settings such as in complete darkness, in smoke, fog or dust, episodes of adverse weather such as snow or rain, or areas of dense undergrowth, snow cover or while submerged. It should also be added that information commonly displayed on military "dog tags" may be disposed on the illuminated display system 300 of FIG. 27.

In a further illustration, consider the following scenario with mass casualties such as among others in natural disaster conditions, casualties arising from terrorism including bioterrorism and terrorism using chemical agents, and accidents involving a plurality of injured users in the context of administrating medical care to a particular injured user with respect to a injured group. Accordingly, a brief clinical assessment is administered to the injured user. The illuminated display system 300 as discussed in detail above is secured to the injured user to assist in prioritizing the degree of medical care administered relative to an injured group. The selector 330 of the illuminated display system 300 is adjusted to designate a desired light emitter from the plurality of light emitters 317. In one exemplary embodiment, the selector 330 in conjunction with the control system 335 executes a sequence by which a desired light emitter is selected from the plurality of light emitters 317 including, among others, light emitters that provide an infrared wavelength band of light, an intermittent infrared wavelength band of light, a red wavelength band of visible light, a green wavelength band of visible light, a blue wavelength band of visible light, and white wavelength band of visible light. Accordingly, the selector 330 applies a voltage to the desired light emitter for activation thereof. The light emitter is illuminated at the desired predetermined wavelength to provide information relating to the degree of injury of the injured user with respect to the injured group.

Although the present invention has been described in detail, it should be understood that various changes, substitutions, and alterations could be made hereto without departing from the spirit and scope of the invention as defined by the appended claims.

I claim:

1. An illuminated display system for placement on a user, the illuminated display system comprising:

a base assembly, the base assembly including a base body having a top portion and a bottom portion, a fastening interface positioned at the bottom portion of the base body, the fastening interface operatively coupled to the user, and a display interface disposed on the top portion of the base body, the display interface including a plurality of light emitters, each light emitter from the plurality of light emitters providing a different predetermined wavelength of light than the other light emitters from the plurality of light emitters, each respective predetermined wavelength providing information relating to a corresponding predetermined status of the user; and a dial assembly operatively coupled to the base assembly, the dial assembly including a selector to activate a desired light emitter from the plurality of light emitters, the selector applies a voltage to the desired light emitter for illumination thereof.

2. The illuminated display system according to claim 1 wherein the fastening interface comprises a loop assembly.

3. An illuminated display system for prioritizing medical care administered to an injured user with respect to a plurality of injured users, the illuminated display system comprising:

a base assembly, the base assembly including a base body having a first portion and a display interface disposed on the first portion of the base body, the display interface including a plurality of light emitters, each light emitter from the plurality of light emitters providing a different predetermined wavelength of light than the other light emitters from the plurality of light emitters, each respective predetermined wavelength providing information relating to the degree of injury of the injured user with respect to the plurality of injured users; and a dial assembly operatively coupled to the base assembly, the dial assembly including a selector to activate a desired light emitter from the plurality of light emitters, the selector applies a voltage to the desired light emitter for illumination thereof.

4. The illuminated display system according to claim 3 further including a control system coupled to the plurality of light emitters.

5. The illuminated display system according to claim 3 wherein the base body further includes a second portion and wherein the illuminated display system further includes a fastening interface positioned at the second portion of the base body, the fastening interface operatively coupled to the user.

6. An illuminated display system for prioritizing medical care, the illuminated display system comprising:

a base assembly, the base assembly including a base body and a display interface disposed on the base body, the display interface including a plurality of light emitters, each light emitter from the plurality of light emitters providing a different predetermined wavelength of light than the other light emitters from the plurality of light emitters, each respective predetermined wavelength providing information relating to the degree of injury of a soldier; and a selector coupled to the base assembly, the selector receives a manual input and activates a desired light emitter having a different wavelength from the plurality of light emitters based on the manual input, the selector applies a voltage to the desired light emitter for illumination thereof as related to the degree of injury of the soldier, the degree of injury is prioritized in the context of administering medical care to the injured soldier in battlefield settings.

7. An illuminated display system according to claim 6 wherein the plurality of light emitters includes a light emitting diode.

8. An illuminated display system according to claim 7 wherein the light emitting diode comprises an organic light emitting diode.

9. An illuminated display system according to claim 7 wherein the light emitting diode provides an infrared wavelength band of light.

10. An illuminated display system according to claim 7 wherein the light emitting diode intermittently provides an infrared wavelength band of light.

11. An illuminated display system according to claim 7 wherein the light emitting diode provides a red wavelength band of visible light.

12. An illuminated display system according to claim 7 wherein the light emitting diode provides a green wavelength band of visible light.

13. At illuminated display system according to claim 7 wherein the light emitting diode provides a blue wavelength band of visible light.

14. An illuminated display system according to claim 6 further including a control system coupled to the plurality of light emitters.

15. An illuminated display system according to claim 14 wherein the control system adjusts the intensity of the light produced by at least one light emitter of the plurality of light emitters.

16. An illuminated display system according to claim 14 wherein the control system adjusts the duration of light signal produced by at least one light emitter of the plurality of light emitters.

17. An illuminated display system according to claim 6 further including a plurality of interchangeable dial lenses, and wherein each interchangeable dial lens from the plurality of interchangeable dial lens is releaseably coupled to the base assembly.

18. An illuminated display system for placement on a user, the illuminated display system comprising:

a base assembly, the base assembly including a base body, a fastening interface extending from the base body, the fastening interface operatively coupled to the user, and a display interface disposed on the base body, the display interface including a plurality of light emitters, each light emitter from the plurality of light emitters providing a different predetermined wavelength of light than the other light emitters from the plurality of light emitters, each respective predetermined wavelength providing information relating to a corresponding predetermined status of the user; and a selector electrically coupled to the base assembly and activating a desired light emitter from the plurality of light emitters, the selector receives at least one manual input from the user and applies a voltage to the desired light emitter for illumination thereof.

19. An illuminated display system for prioritizing medical care administered to an injured user with respect to a plurality of injured users, the illuminated display system comprising:

a base assembly, the base assembly including a base body and a display interface disposed on the base body, the display interface including a plurality of light emitters, each light emitter from the plurality of light emitters providing a different predetermined wavelength of light than the other light emitters from the plurality of light emitters, each respective predetermined wavelength providing information relating to the degree of injury of the injured user with respect to the plurality of injured users; and a selector coupled to the base assembly, the selector receives a manual input and activates a desired light emitter from the plurality of light emitters based on the manual input, the selector applies a voltage to the desired light emitter for illumination thereof as related to the degree of injury of the injured user, thereby the degree of injury is prioritized in the context of administering medical care to the injured user based on the illuminated light emitter.

20. An illuminated display system according to claim 19 wherein each light emitting diode provides different band of colored light substantially within the wavelength of visible light.

* * * * *